US012575716B2

(12) United States Patent
Katayama

(10) Patent No.: US 12,575,716 B2
(45) Date of Patent: Mar. 17, 2026

(54) ENDOSCOPE

(71) Applicant: HOYA CORPORATION, Tokyo (JP)

(72) Inventor: Toshiyuki Katayama, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 836 days.

(21) Appl. No.: 17/274,300

(22) PCT Filed: Feb. 10, 2020

(86) PCT No.: PCT/JP2020/005056
§ 371 (c)(1),
(2) Date: Mar. 8, 2021

(87) PCT Pub. No.: WO2020/202801
PCT Pub. Date: Oct. 8, 2020

(65) Prior Publication Data
US 2021/0338061 A1 Nov. 4, 2021

(30) Foreign Application Priority Data

Mar. 29, 2019 (JP) ................................. 2019-068547

(51) Int. Cl.
*A61B 1/00* (2006.01)
*A61B 1/005* (2006.01)
(52) U.S. Cl.
CPC ........ *A61B 1/00126* (2013.01); *A61B 1/0057* (2013.01); *A61B 1/00195* (2013.01)
(58) Field of Classification Search
CPC .............. A61B 1/00126; A61B 1/0057; A61B 1/00195; A61B 1/00188; A61B 1/00096; A61B 1/0019; A61B 1/05; G02B 7/04
See application file for complete search history.

(56) References Cited

U.S. PATENT DOCUMENTS 5,993,381 A 11/1999 Ito
6,117,071 A * 9/2000 Ito ............................ A61B 1/05
600/129

(Continued)

FOREIGN PATENT DOCUMENTS

CN 207742400 U * 8/2018
DE 198 37 404 A1 2/1999

(Continued)

OTHER PUBLICATIONS

JP 3360799 Attached as an equivalent translation to JPH1147075A furnished by the EPO.*

(Continued)

*Primary Examiner* — Michael J Carey
*Assistant Examiner* — Timothy Tuan Luu
(74) *Attorney, Agent, or Firm* — Greenblum & Bernstein, P.L.C.

(57) ABSTRACT

Provided is an endoscope capable of suppressing the displacement of a movable optical frame due to bending of a bending portion. An endoscope according this embodiment includes an insertion portion that includes a distal end portion, a bending portion, and a soft portion in order from the distal end side, a movable optical frame that is built in the distal end portion and capable of advancing and retreating in an axial length direction of the insertion portion, an operation coil that is connected to the movable optical frame and capable of advancing and retreating in the axial length direction of the insertion portion, and a protection coil through which the operation coil is inserted and which penetrates at least the bending portion.

12 Claims, 11 Drawing Sheets

(56)                     References Cited

U.S. PATENT DOCUMENTS

| | | | |
|---|---|---|---|
| 6,409,658 B1 | 6/2002 | Mitsumori | |
| 6,422,995 B2 * | 7/2002 | Akiba ................ | A61B 1/00188 |
| | | | 600/168 |
| 2009/0076332 A1 * | 3/2009 | Iwasaki ............. | A61B 1/00094 |
| | | | 600/168 |

FOREIGN PATENT DOCUMENTS

| | | | | |
|---|---|---|---|---|
| DE | 10055726 A1 * | 6/2001 | ......... | A61B 1/00098 |
| JP | H06-209944 A | 8/1994 | | |
| JP | 07-163513 | 6/1995 | | |
| JP | 11-47075 | 2/1999 | | |
| JP | 11-311744 | 11/1999 | | |
| JP | 11311744 A * | 11/1999 | | |
| JP | 2000-180734 | 6/2000 | | |
| JP | 3360799 B2 * | 12/2002 | ......... | A61B 1/00059 |
| JP | 2005287576 A * | 10/2005 | | |
| JP | 2016-054967 | 4/2016 | | |
| JP | 2016054967 A * | 4/2016 | | |
| WO | WO-2016203626 A1 * | 12/2016 | ......... | A61B 1/00006 |

OTHER PUBLICATIONS

Official Communication issued in International Bureau of WIPO Patent Application No. PCT/JP2020/005056, dated Apr. 14, 2020.
Office Action issued in German Patent Application No. 11 2020 001 676.5, dated May 4, 2023.

* cited by examiner

ENDOSCOPE

TECHNICAL FIELD

The present invention relates to an endoscope.

BACKGROUND ART

Conventionally, for example, in a medical field, an endoscope having an insertion portion to be inserted into an object to be inserted has been used. The insertion portion has an elongated tubular shape. A light source and an image sensor are built in the distal end side of the insertion portion. The light emitted by the light source illuminates the inside of the object to be inserted, and the image sensor images the inside of the object to be inserted. The image of the inside of the object to be inserted is displayed on a display device, for example. The user observes the inside state of the object to be inserted by watching the displayed image.

A plurality of objective lenses are juxtaposed in the insertion portion in the axial length direction of the insertion portion. The light transmitted through these objective lenses is incident on the image sensor.

Further, a wire is inserted into the insertion portion from the proximal end to the distal end portion of the insertion portion. The distal end portion of the wire is connected to a movable optical frame that holds one objective lens. When the wire advances and retreats in the axial length direction of the insertion portion, the movable optical frame comes into contact with and separates from the other objective lens fixed to the tip of the insertion portion in the axial length direction of the insertion portion. As a result, the focal length of the optical system is adjusted.

The wire is inserted into a tightly wound coil so that the other member arranged in the insertion portion and the wire do not interfere with each other. This type of endoscope is disclosed in, for example, Patent Literature 1.

CITATION LIST

Patent Literature

Patent Literature 1: JP 11-47075 A

SUMMARY OF INVENTION

Technical Problem

The insertion portion has a bending portion. The bending portion is bent/straightened by the operation of the user.

The tightly wound coil penetrates at least the bending portion. Both end portions of the tightly wound coil are fixed in the axial length direction of the insertion portion. When the movable optical frame is positioned, the proximal end of the wire is also fixed in the axial length direction of the insertion portion.

As the bending portion bends, the tightly wound coil also bends. The outer peripheral side of the bent tightly wound coil extends relative to the inner peripheral side. Since the wire has no elasticity, the wire is pulled inside the tightly wound coil toward the proximal end side of the tightly wound coil as the tightly wound coil bends. Therefore, the movable frame body positioned when the bending portion is straightened is displaced to one side in the axial length direction as the bending portion bends. Similarly, the movable frame body positioned when the bending portion bends is displaced to the other side in the axial length direction as the bending portion is stretched.

The displacement of the movable frame means an unnecessary change in the focal length, which is inconvenient.

The present invention has been made in view of such circumstances, and a main object thereof is to provide an endoscope capable of suppressing a displacement of the movable optical frame due to a bending of the bending portion.

Solution to Problem

An endoscope according to this embodiment includes an insertion portion that includes a distal end portion, a bending portion, and a soft portion in order from the distal end side, a movable optical frame that is built in the distal end portion and capable of advancing and retreating in an axial length direction of the insertion portion, an operation coil that is connected to the movable optical frame and capable of advancing and retreating in the axial length direction of the insertion portion, and a protection coil through which the operation coil is inserted and which penetrates at least the bending portion.

In this embodiment, when the operation coil advances and retreats in the axial length direction of the insertion portion, the movable optical frame connected to the operation coil advances and retreats in the axial length direction of the insertion portion.

The operation coil is inserted through the protection coil. When the bending portion has bent, the protection coil and the operation coil also bend.

The protection coil has elasticity, and the outside of the bending portion expands and contracts relatively to the inside of the bending portion as it bends. The same applies to the operation coil.

That is, since the operation coil expands and contracts at the same time as the expansion and contraction of the protection coil, there is no possibility that the position of the operation coil in the axial length direction is relatively displaced with respect to the protection coil at the time of bending.

Therefore, it is possible to suppress the displacement of the movable optical frame due to the bending of the bending portion.

In the endoscope according to this embodiment, the distal end portion of the operation coil and the movable optical frame are connected via a wire whose outer diameter is smaller than the outer diameter of the operation coil.

In this embodiment, it is possible to reduce the force required for bending the bending portion by utilizing the fact that the thin wire is more easily bent than the thick operation coil.

Further, the movable optical frame can be smoothly moved forward and backward by utilizing the fact that the frictional force of the wire is smaller than the frictional force of the operation coil with respect to the protection coil.

As a result, the operability of the endoscope can be improved.

In the endoscope according to this embodiment, the operation coil and the movable optical frame are connected via a tubular cam surrounding the movable optical frame, and advancing/retreating of the operation coil, forward/reverse rotation of the cam in a circumferential direction, and advancing/retreating of the movable optical frame are linked.

In this embodiment, the advancing/retreating of the operation coil, the forward/reverse rotation of the tubular cam in the circumferential direction, and the advancing/retreating of the movable optical frame are linked. Therefore, depending on the shape of the cam, the advance (or retreat) of the operation coil and one (or the other) of the advance and retreat of the movable optical frame can be interlocked.

In the endoscope according to this embodiment, the pitch of the operation coil and the pitch of the protection coil are equal to each other.

In this embodiment, since the pitch of the operation coil and the pitch of the protection coil are equal to each other, the strands of the operation coil are likely to engage between the strands of the protection coil. Therefore, it is possible to further suppress the displacement of the operation coil in the axial length direction of the protection coil.

In the endoscope according to this embodiment, the advancing/retreating of the operation coil corresponds to retreating/advancing of the movable optical frame. The operation coil urges the movable optical frame in a backward direction. A traction portion for retracting the operation coil by traction is provided.

In this embodiment, the movable optical frame is usually arranged on the proximal end side of the range of motion due to the urging of the operation coil. When the operation coil is pulled using the traction portion, the operation coil retracts. As the operation coil retracts, the movable optical frame advances toward the distal end side of the range of motion.

The operation coil that is pressed is easy to bend, but the operation coil that is pulled is hard to bend. Therefore, the force required for the movable optical frame to advance can be reliably transmitted.

Since the operation coil has the force required for the movable optical frame to retreat, the user does not need to press the operation coil.

Since the operation coil also serves as a member for urging the movable optical frame in the backward direction, the number of parts is reduced. In addition, the size of the endoscope can be reduced.

In the endoscope according to this embodiment, the traction portion is provided in an operation unit to which the proximal end side of the soft portion is connected.

In this embodiment, the traction portion is provided in the operation unit. The user can move the movable optical frame forward and backward by operating the traction portion.

In the endoscope according to this embodiment, the strand of the operation coil is a flat wire.

In this embodiment, since the strand of the operation coil is a flat wire, the diameter of the operation coil can be reduced.

In the endoscope according to this embodiment, the operation coil is a tightly wound coil.

In this embodiment, since the operation coil is a tightly wound coil, it is possible to prevent the operation coil and the protection coil from being entangled with each other.

In the endoscope according to this embodiment, the protection coil is a tightly wound coil. A strand of the operation coil and a strand of the protection coil are the same as each other.

In this embodiment, since the operation coil and the protection coil are each tightly wound coils, it is further suppressed that the operation coil and the protection coil are entangled with each other.

Since the strand of the operation coil and the strand of the protection coil are the same, the pitch of both can be the same.

Advantageous Effects of Invention

According to the endoscope of this embodiment, it is possible to suppress the displacement of the movable optical frame due to the bending of the bending portion.

BRIEF DESCRIPTION OF DRAWINGS

FIG. 13 is a schematic view of the operation coil and the protection coil when an insertion portion is curved and looped.

DESCRIPTION OF EMBODIMENTS

Hereinafter, the present invention will be specifically described with reference to the drawings illustrating embodiments of the invention.

First Embodiment

Figure 1:
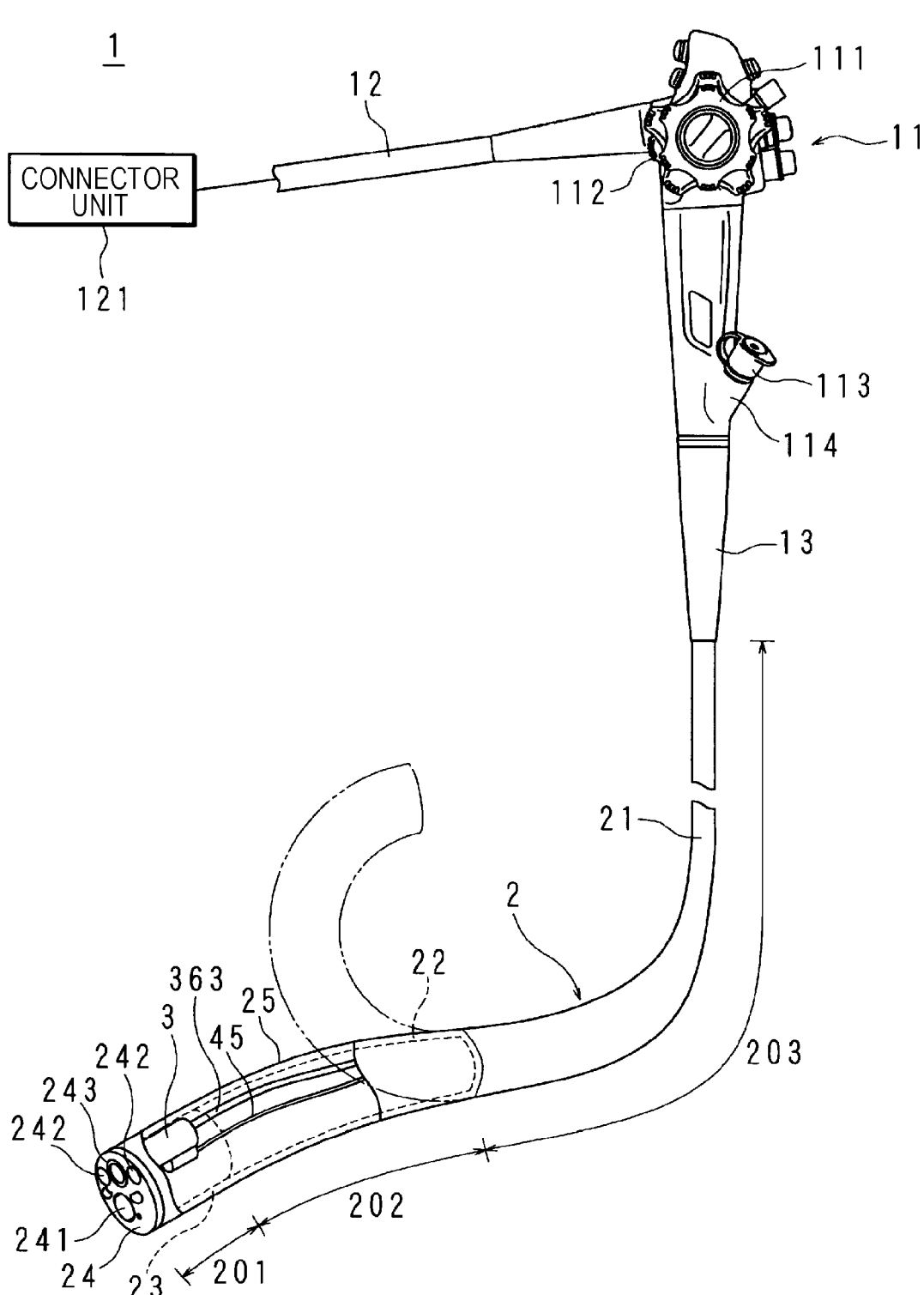
FIG. 1 is an exterior view of an endoscope according to a first embodiment.

FIG. 1 is an exterior view of an endoscope of a first embodiment.

In the drawing, 1 indicates an endoscope, and the endoscope 1 is a flexible scope for the upper gastrointestinal tract or the lower gastrointestinal tract. The endoscope 1 includes an operation unit 11, a universal cord 12, and an insertion portion 2.

The operation unit 11 has a rigid housing. An operation knob 111 and an operation lever 112 operated by the user are provided on the outer surface of the housing of the operation unit 11. Further, a channel inlet 114 closed by a forceps plug 113 is provided on the outer surface of the housing of the operation unit 11.

The universal cord 12 is connected to one side of the operation unit 11. Power lines and signal lines (not illustrated) are wired from the universal cord 12 to the insertion portion 2. By connecting a connector unit 121 provided at the distal end portion of the universal cord 12 to a power source device, a display device, etc. (not illustrated), the power line and the signal line of the endoscope 1 are electrically connected to the power source device, the display device, etc.

The insertion portion 2 has an elongated tubular shape and extends from the other side of the operation unit 11. In the following, the side of the insertion portion 2 near the operation unit 11/the side far from the operation unit 11 is referred to as the proximal end side/distal end side. A bend preventing portion 13 for protecting the proximal end of the insertion portion 2 is provided between the insertion portion 2 and the operation unit 11.

The insertion portion 2 has a distal end portion 201, a bending portion 202, and a soft portion 203 in this order from the distal end side. The distal end portion 201 is the shortest and hardest. The bending portion 202 has flexibility. The length of the bending portion 202 is appropriately determined in the range of, for example, 80 mm to 120 mm. The soft portion 203 is the longest and flexible.

The soft portion 203 of the insertion portion 2 is covered with a flexible soft tube 21.

The bending portion 202 of the insertion portion 2 includes a bending tube 22 that has flexibility and can be bent/straightened. The proximal end of the bending tube 22 is covered with the distal end portion of the soft tube 21.

A plurality of operating wires (not illustrated) are connected to the bending tube 22 of the bending portion 202. These operating wires extend over the entire length of each of the soft portion 203 and the bending portion 202, and the proximal end of each operating wire is connected to the operation unit 11. By operating the operation knob 111 of the operation unit 11, the operating wires are individually moved forward and backward. As a result, the bending portion 202 is deformed flexibly.

The distal end portion 201 of the insertion portion 2 includes a distal end cylinder 23 and a cap 24.

The distal end cylinder 23 is hard. The distal end portion of the bending tube 22 of the bending portion 202 is coaxially connected to the proximal end of the distal end cylinder 23.

The outer peripheral surfaces of the bending tube 22 and the distal end cylinder 23 are each covered with a soft cover tube 25.

The cap 24 is hard. The cap 24 is fixed to the distal end cylinder 23 and closes the opening on the distal end side of the cover tube 25.

The cap 24 is provided with a channel outlet 241. The channel outlet 241 and the channel inlet 114 of the operation unit 11 communicate with each other by a channel tube (not illustrated).

The cap 24 is provided with two windows 242 and 242. Illumination lenses are fitted in the windows 242 and 242, and light sources are arranged facing each illumination lens (not illustrated).

The cap 24 is provided with an opening 243. The opening 243 is arranged between the windows 242 and 242.

Figure 2:
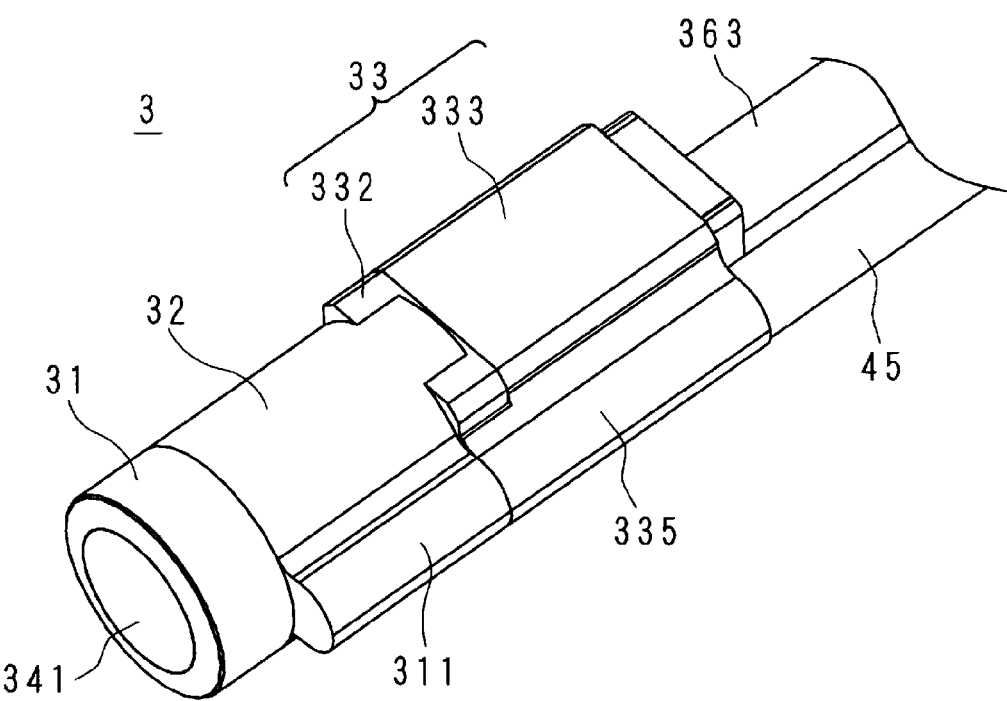
FIG. 2 is a perspective view of an imaging unit.

FIG. 2 is a perspective view of an imaging unit 3.

Figure 3:
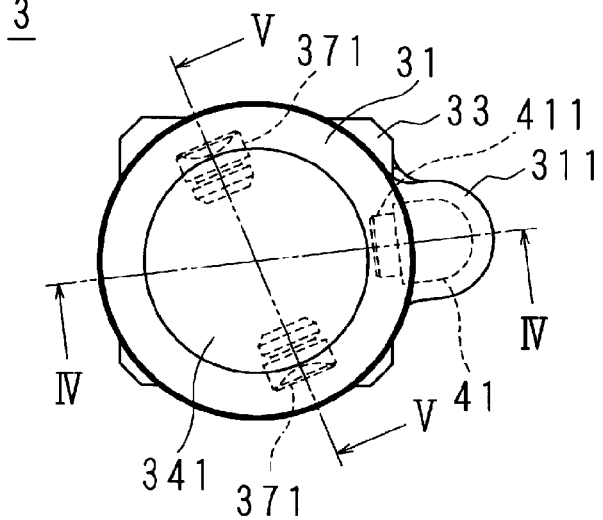
FIG. 3 is a front view of the imaging unit.

FIG. 3 is a front view of the imaging unit 3.

The imaging unit 3 includes an objective case 31, a lens case 32, and an image pickup case 33 in this order from the distal end side of the insertion portion 2 (see FIG. 1).

Figure 4:
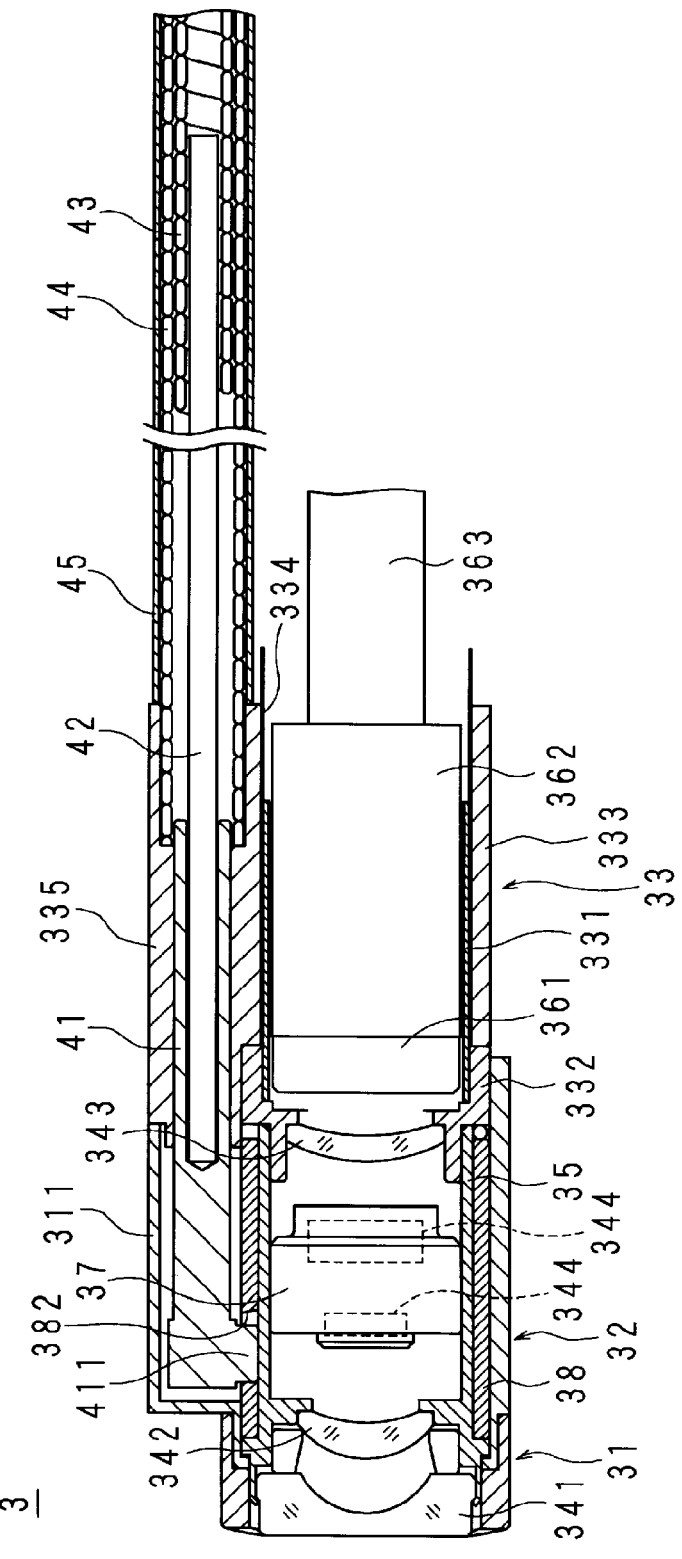
FIG. 4 is a cross-sectional view of the imaging unit taken along line IV-IV in FIG. 3.

FIG. 4 is a cross-sectional view of the imaging unit 3 taken along line IV-IV in FIG. 3.

Figure 5:
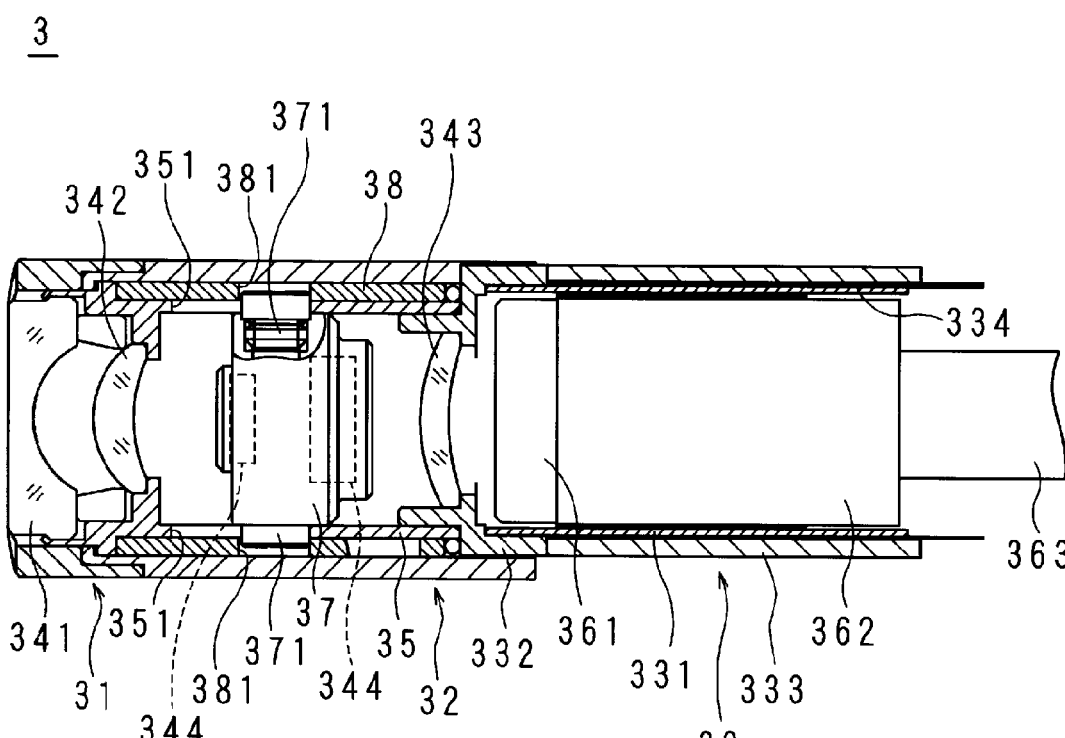
FIG. 5 is a cross-sectional view of the imaging unit taken along line V-V in FIG. 3.

FIG. 5 is a cross-sectional view of the imaging unit 3 taken along the line V-V in FIG. 3.

The objective case 31, the lens case 32, and the image pickup case 33 illustrated in FIG. 2 to FIG. 5 each have a tubular shape. These axial length directions are along the axial length direction of the insertion portion 2.

The objective case 31 holds an objective lens 341. The objective lens 341 closes the opening on the distal end side of the objective case 31. The distal end portion of the lens case 32 is internally fitted to the proximal end of objective case 31.

A tubular objective frame 35 is internally fitted in the lens case 32.

Figure 6:
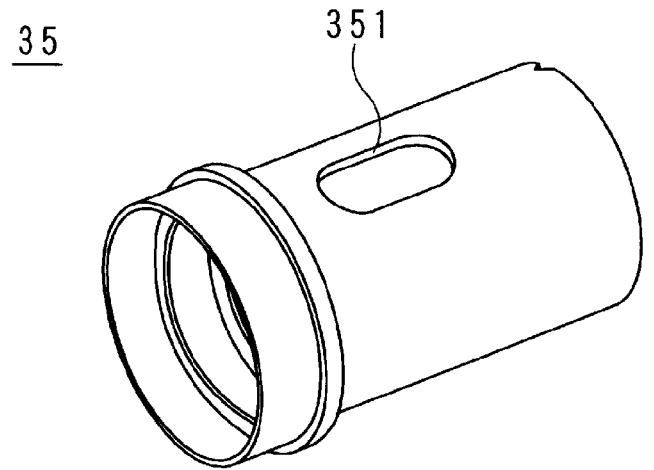
FIG. 6 is a perspective view of an objective frame.

FIG. 6 is a perspective view of the objective frame 35.

The objective frame 35 illustrated in FIG. 4 to FIG. 6 holds an objective lens 342. The objective lens 342 closes the opening on the distal end side of the objective frame 35. The proximal end of the objective frame 35 is also internally fitted to the proximal end of the objective case 31.

The image pickup case 33 illustrated in FIG. 2 to FIG. 5 includes a tubular shield pipe 331, a tubular lens holding frame 332, and a tubular case body 333.

The proximal end of the lens holding frame 332 is externally fitted to the distal end portion of the shield pipe 331. The portion other than the distal end portion of the shield pipe 331 is internally fitted into the case body 333 via the resin layer 334. The distal end portion of the lens holding frame 332 is internally fitted into the proximal end of the objective frame 35.

The objective case 31, the lens case 32, and the image pickup case 33 integrated as described above are arranged at the distal end portion 201 (see FIG. 1) of the insertion portion 2.

The lens holding frame 332 holds an objective lens 343. The objective lens 343 closes the opening on the distal end side of the lens holding frame 332.

An image sensor 361 and a driver IC 362 are housed in the shield pipe 331 of the image pickup case 33.

The image sensor 361 is, for example, a CMOS image sensor. The light receiving portion of the image sensor 361 faces the objective lens 343.

The driver IC 362 is, for example, a CMOS-IC. The driver IC 362 is electrically connected to the image sensor 361 and drives the image sensor 361.

The driver IC 362 is electrically connected to one end portion of a cable 363. The cable 363 has a structure in which the above-mentioned power line and signal line are covered with a sheath, and has pliability capable of following the deformation of each of the soft tube 21 and the bending tube 22. The cable 363 extends from the opening on the proximal end side of the shield pipe 331 toward the proximal end side of the bending tube 22 illustrated in FIG. 1, and extends to the connector unit 121 of the universal cord 12.

A part of the power line of the cable 363 is drawn from the distal end portion of the cable 363, and connected to the above-mentioned light source (not illustrated).

The cable 363 is used for supplying power from the above-mentioned power source device to the image sensor 361 and the light source, and outputting a signal from the image sensor 361 to the display device.

As illustrated in FIG. 4 and FIG. 5, a movable optical frame 37 is held inside the objective frame 35.

The movable optical frame 37 has a tubular shape. The movable optical frame 37 is slidably fitted in the objective frame 35 on the inner surface of the objective frame 35.

The movable optical frame 37 holds a plurality of objective lenses 344, 344, and so on.

As a result of the above, the objective lens 341, the objective lens 342, the objective lenses 344, 344 . . . , and the objective lens 343 are juxtaposed in the axial length direction of the insertion portion 2 in this order from the distal end side. The optical axis of these objective lens groups is along the axial length direction of the insertion portion 2.

The number of objective lenses 344 held by the movable optical frame 37 is not limited to a plurality, and may be one.

Two cam pins 371 and 371 project outward from the outer circumference of the movable optical frame 37. The cam pins 371 and 371 are separated from each other by 180° in the circumferential direction of the movable optical frame 37 (see FIG. 3).

The objective frame 35 is provided with two guiding grooves 351 and 351 (see FIG. 6). The guiding grooves 351 and 351 are separated from each other by 180° in the circumferential direction of the objective frame 35. Each guiding groove 351 penetrates the peripheral wall of the objective frame 35 and extends in the axial length direction of the objective frame 35, accordingly in the axial length direction of the insertion portion 2.

The cam pins 371 and 371 of the movable optical frame 37 are inserted into the guiding grooves 351 and 351 of the objective frame 35. By guiding the cam pins 371 and 371 to the guiding grooves 351 and 351, the movable optical frame 37 can move forward and backward in the axial length direction of the insertion portion 2.

Figures 7, 8:
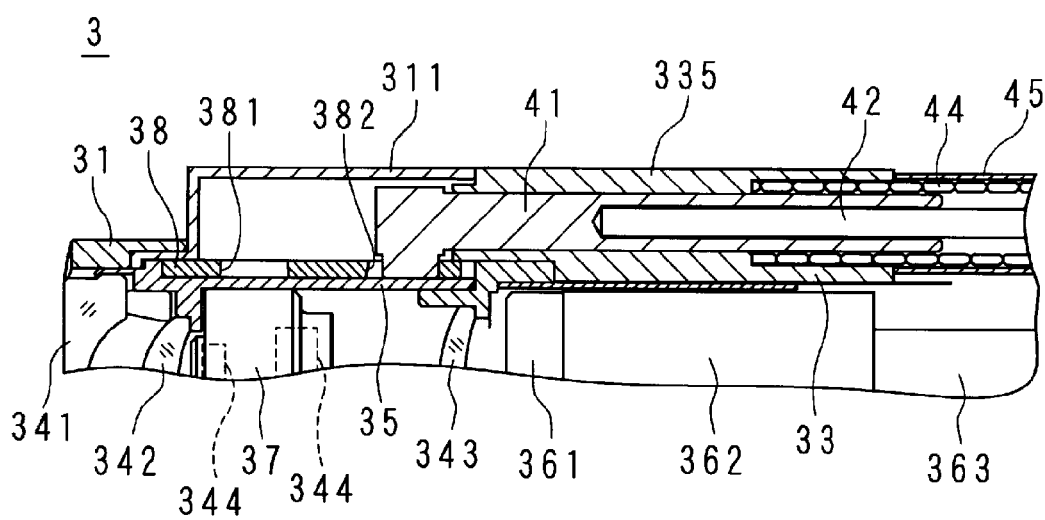
FIG. 7 is an enlarged cross-sectional view of the imaging unit.
FIG. 8 is a perspective view of a cam.

FIG. 7 is an enlarged cross-sectional view of the imaging unit 3 (see line IV-IV in FIG. 3).

FIG. 7 illustrates a state in which the movable optical frame 37 is located at the distal end of the movable range.

On the other hand, FIG. 4 and FIG. 5 illustrate a state in which the movable optical frame 37 is located at the proximal end of the movable range.

As illustrated in FIG. 4, FIG. 5, and FIG. 7, as the movable optical frame 37 moves forward/backward, the objective lenses 344, 344, . . . held in the movable optical frame 37 come into contact with/detach from the objective lenses 341 and 342, and detach from/contact with the objective lens 343.

When the objective lenses 344, 344, . . . are close to the objective lenses 341 and 342 and separated from the objective lenses 343, the focal lengths of these objective lens groups are long. On the other hand, when the objective lenses 344, 344, . . . are separated from the objective lenses 341 and 342 and are close to the objective lens 343, the focal lengths of these objective lens groups are short.

A cam 38 is held on the outside of the objective frame 35.

The cam 38 has a tubular shape. The cam 38 is slidably fitted to the outer surface of the objective frame 35 in the outer surface of the objective frame 35.

FIG. 8 is a perspective view of the cam 38.

Figure 9:
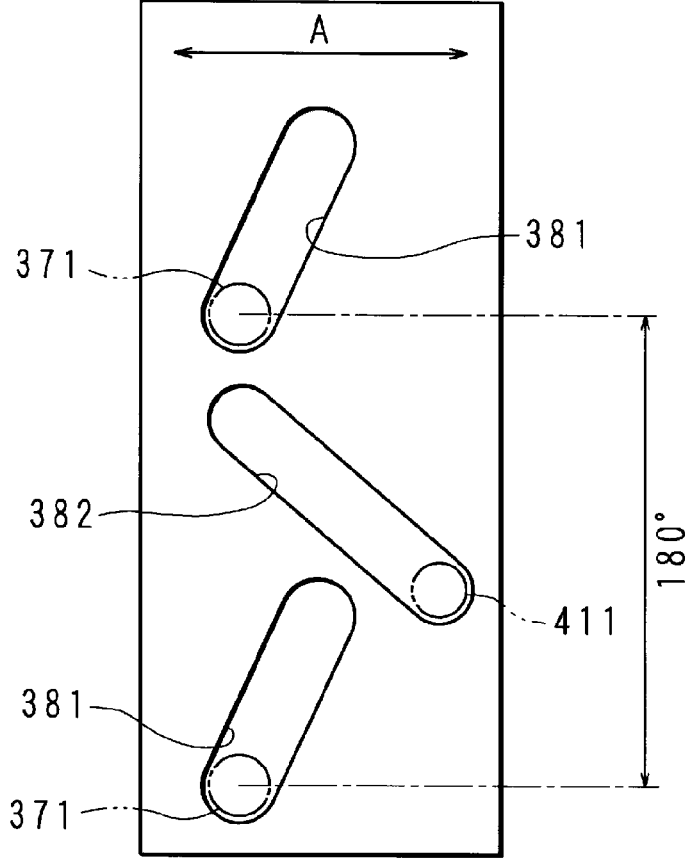
FIG. 9 is a development view of the cam.

FIG. 9 is a development view of the cam 38. The arrow A illustrated in FIG. 9 indicates the axial length direction of the insertion portion 2.

The cam 38 illustrated in FIG. 4, FIGS. 5, and 7 to FIG. 9 is provided with two cam grooves 381 and 381 and a cam groove 382.

The cam grooves 381 and 381 are separated from each other by 180° in the circumferential direction of the cam 38. Each cam groove 381 penetrates the peripheral wall of the cam 38, and extends in a direction inclined with respect to the axial length direction of the cam 38, accordingly the axial length direction of the insertion portion 2. The longitudinal directions of the cam grooves 381 and 381 are along each other.

The cam groove 382 penetrates the peripheral wall of the cam 38, is inclined in the axial length direction of the cam 38, and extends in a direction inclined with respect to the longitudinal direction of the cam grooves 381 and 381.

The cam pins 371 and 371 of the movable optical frame 37 are inserted into the cam grooves 381 and 381.

When the cam 38 rotates to one side in the circumferential direction (hereinafter, referred to as forward rotation), the movable optical frame 37 is advanced by guiding the cam pins 371 and 371 to the cam grooves 381 and 381 and the guiding grooves 351 and 351 of the objective frame 35. On the other hand, when the cam 38 rotates to the other side in the circumferential direction (hereinafter, referred to as backward rotation), the movable optical frame 37 is retracted by guiding the cam pins 371 and 371 to the cam grooves 381 and 381 and the guiding grooves 351 and 351 of the objective frame 35.

The imaging unit 3 includes a slider 41.

Figure 10:
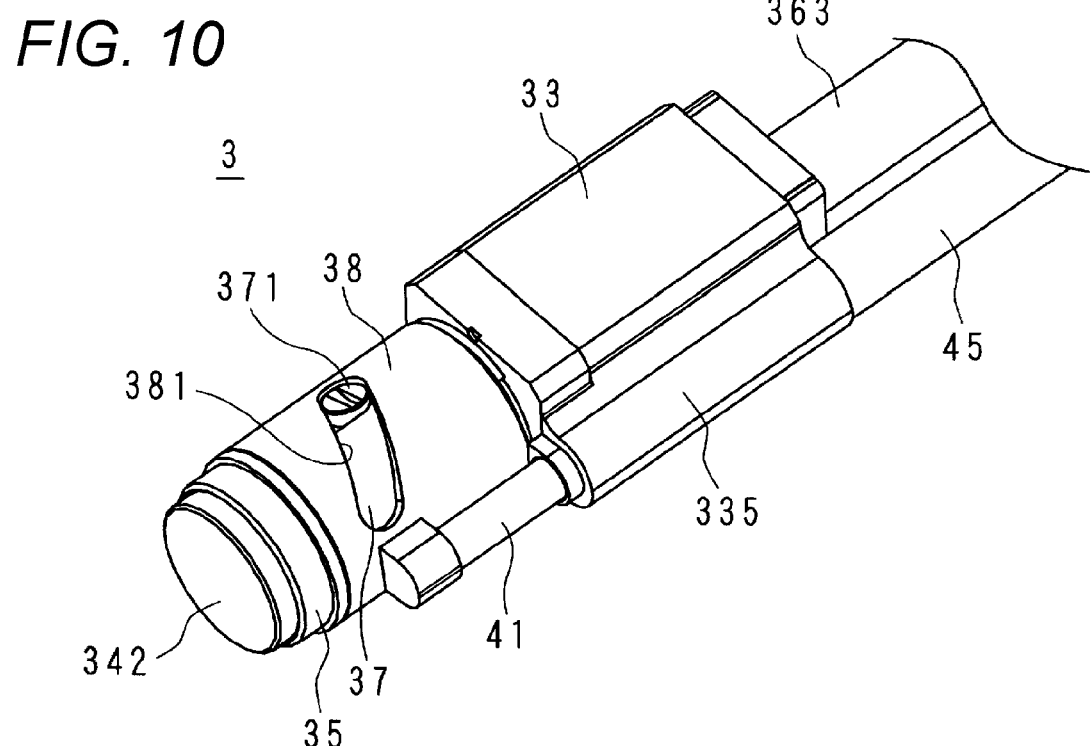
FIG. 10 is a perspective view of the imaging unit (when a slider is advanced) in which an objective case and a lens case are omitted.

FIG. 10 is a perspective view of the imaging unit 3 (when the slider 41 is advanced) in which the objective case 31 and the lens case 32 are omitted.

Figure 11:
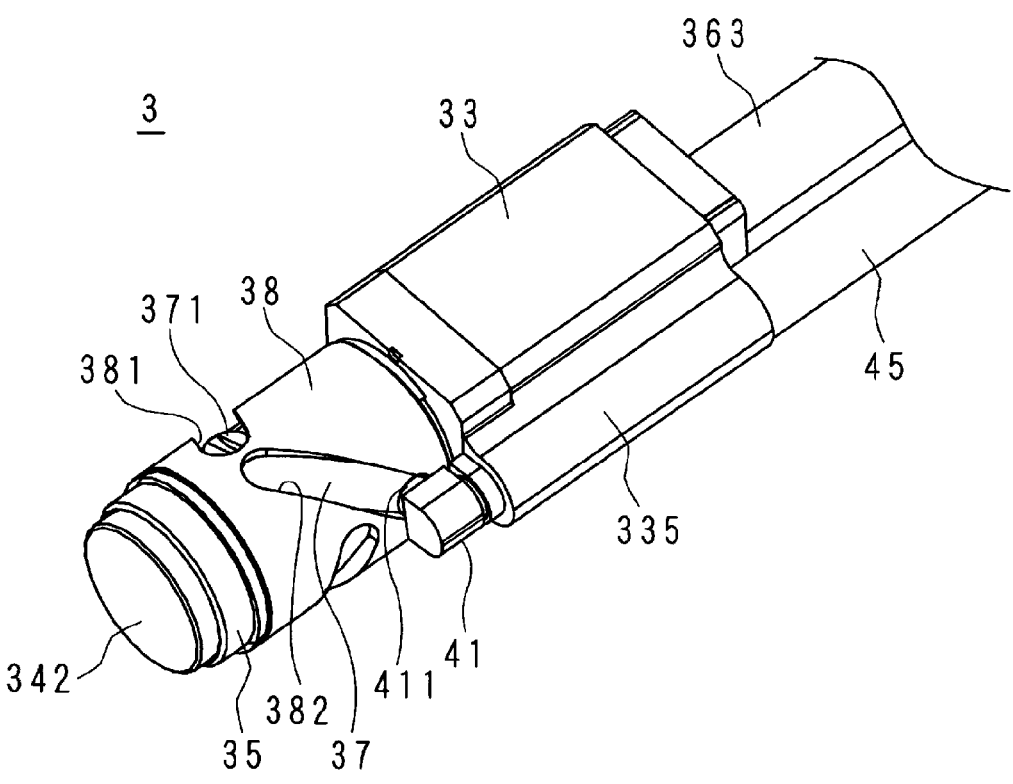
FIG. 11 is a perspective view of the imaging unit (when the slider is retracted) in which the objective case and the lens case are omitted.

FIG. 11 is a perspective view of the imaging unit 3 (when the slider 41 is retracted) in which the objective case 31 and the lens case 32 are omitted.

The slider 41 illustrated in FIG. 4, FIG. 7, FIG. 10, and FIG. 11 has a rod shape. The slider 41 is used with its longitudinal direction oriented in the axial length direction of the insertion portion 2.

A cam follower 411 is provided at the distal end portion of the slider 41. The cam follower 411 is a protrusion that projects in a direction orthogonal to the longitudinal direction of the slider 41, and is inserted into the cam groove 382 of the cam 38 (see FIG. 9).

When the slider 41 retracts, the cam follower 411 is guided to the cam groove 382, so that the cam 38 rotates forward. On the other hand, when the slider 41 advances, the cam follower 411 is guided to the cam groove 382, so that the cam 38 rotates backward.

The objective case 31 is provided with a slider cover 311 (see FIG. 2 and FIG. 3). The slider cover 311 is provided to project outward from the outer peripheral surface of the objective case 31, and covers the distal end portion of the slider 41. Inside the slider cover 311, the distal end portion of the cam follower 411 moves forward and backward.

The image pickup case 33 is provided with a slider guide 335 (see FIG. 2). The slider guide 335 is provided to project outward from the outer peripheral surface of the image pickup case 33, and has a through hole through which the slider 41 is slidably inserted. The slider 41 is guided by the slider guide 335, and moves forward and backward.

One end portion of the wire 42 is connected to the proximal end of the slider 41. The wire 42 is used with its longitudinal direction oriented toward the axial length direction of the insertion portion 2. The wire 42 penetrates the bending portion 202 of the insertion portion 2. The distal end portion of the wire 42 (the connection portion with the slider 41) is located at the distal end portion 201 of the insertion portion 2. The proximal end of the wire 42 (the connection portion with an operation coil 43 described later) is located at the soft portion 203 of the insertion portion 2. The length of the wire 42 is appropriately determined, for example, in a range of 120 mm to 150 mm. The outer diameter of the wire is, for example, 0.5 mm.

The proximal end of the wire 42 is inserted into the operation coil 43 and fixed to one end portion of the operation coil 43.

The operation coil 43 is used with its longitudinal direction facing the axial length direction of the insertion portion 2. The operation coil 43 is a tightly wound coil. The outer diameter/inner diameter of the operation coil 43 are, for example, 1.0 mm/0.64 mm. The inner diameter of the operation coil 43 is larger than the outer diameter of the wire 42. The wire 42 is more flexible than the operation coil 43.

The operation coil 43 is inserted through a protection coil 44.

Figure 12:
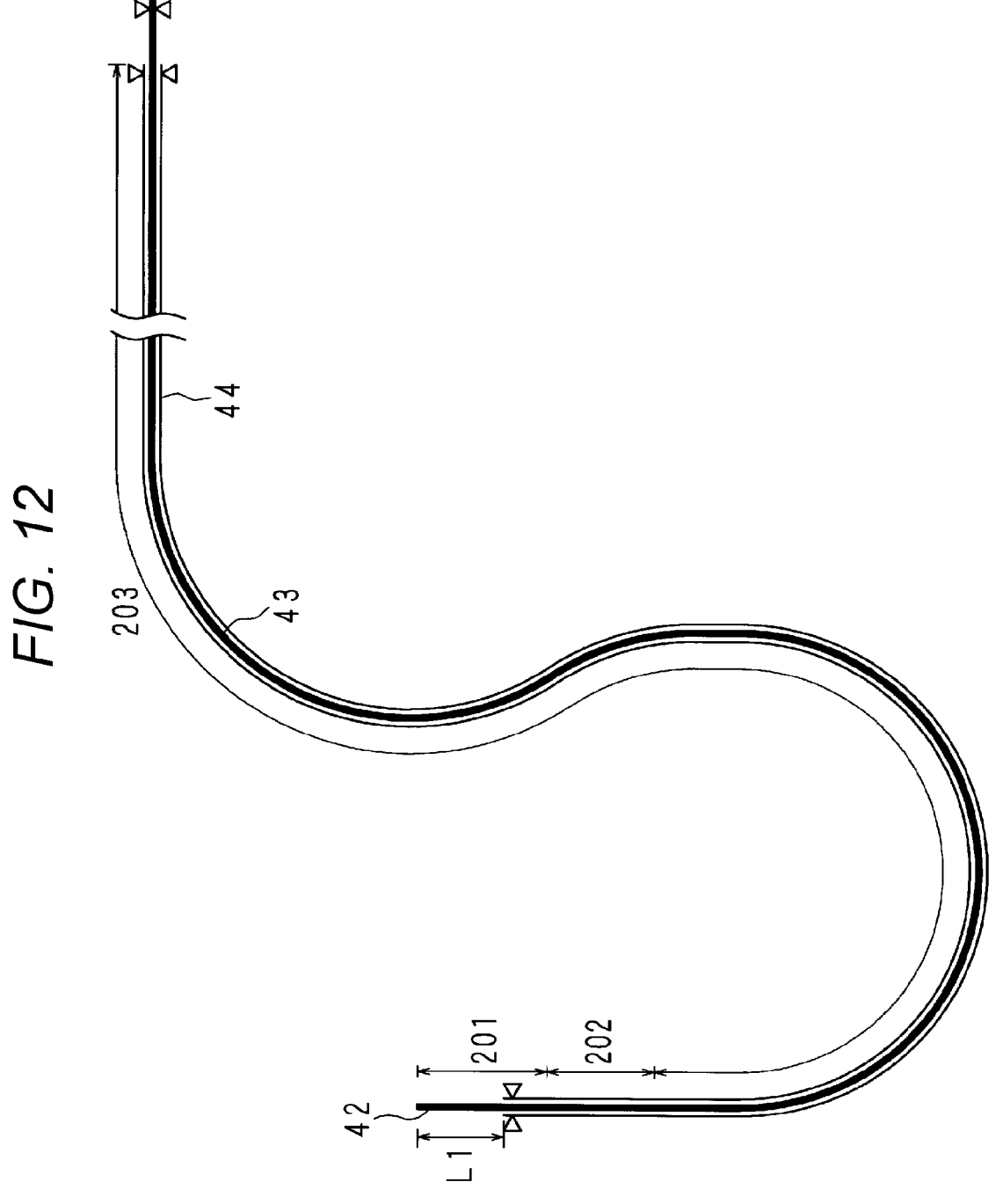
FIG. 12 is a schematic view of an operation coil and a protection coil.

FIG. 12 is a schematic view of the operation coil 43 and the protection coil 44.

The protection coil 44 illustrated in FIG. 4, FIG. 7, and FIG. 12 is used with the longitudinal direction facing the axial length direction of the insertion portion 2. The protection coil 44 is a tightly wound coil. The outer diameter/inner diameter of the protection coil 44 are, for example, 1.46 mm/1.1 mm. There is an appropriate gap between the outer circumference of the operation coil 43 and the inner circumference of the protection coil 44.

The distal end portion of the protection coil 44 is fixed to the slider guide 335 of the image pickup case 33. The protection coil 44 extends over substantially the entire length of the insertion portion 2. The proximal end of the protection coil 44 is fixed to, for example, a fixing portion built in the proximal end of the insertion portion 2.

The operation coil 43 covers substantially the entire length of the insertion portion 2. The proximal end of the operation coil 43 is connected to the operation unit 11. When the operation lever 112 of the operation unit 11 is operated to one side, the operation coil 43 is pulled and retracts while extending. The operation lever 112 functions as a traction portion.

When the operation coil 43 retracts, the slider 41 retracts (see FIG. 11), the cam 38 rotates forward, and the movable optical frame 37 advances (see FIG. 7).

When the operation lever 112 is operated to the other side, the operation coil 43 moves forward while contracting to its original shape due to elasticity.

When the operation coil 43 advances, the slider 41 advances (see FIG. 10), the cam 38 retracts, and the movable optical frame 37 retracts (see FIG. 4 and FIG. 5).

The operation coil 43 also functions as a spring that urges the slider 41 in the forward direction. Since the slider 41 is urged in the forward direction, the cam 38 is urged in the reverse direction and the movable optical frame 37 is urged in the backward direction.

The strands of the operation coil 43 and the protection coil 44 are the same. The strands of the operation coil 43 and the protection coil 44 are flat wires. The strands are not limited to flat wires, and may be round wires, for example. However, in the case of the flat wire, the diameters of the operation coil 43 and the protection coil 44 can be easily reduced as compared with the case of the round wire.

The operation coil 43 and the protection coil 44 are, for example, tightly wound coils having a pitch of 0.485 mm, a rolling plate thickness of 0.18 mm, the number of 1, and a winding direction on the right. Alternatively, the operation coil 43 and the protection coil 44 are, for example, tightly wound coils having a pitch of 0.57 mm, a rolling plate thickness of 0.18 mm, the number of 1, and a winding direction on the right.

Since the operation coil 43 is inserted through the protection coil 44, other members (for example, the cable 363 or the above-mentioned channel tube) arranged in the insertion portion 2 and the protection coil 44 do not interfere with each other. Since the operation coil 43 and the protection coil 44 are both tightly wound coils, both are unlikely to be entangled with each other.

The protection coil 44 is covered with a protection tube 45. The protection tube 45 prevents a foreign matter from entering the inside of the protection coil 44.

Figure 13:
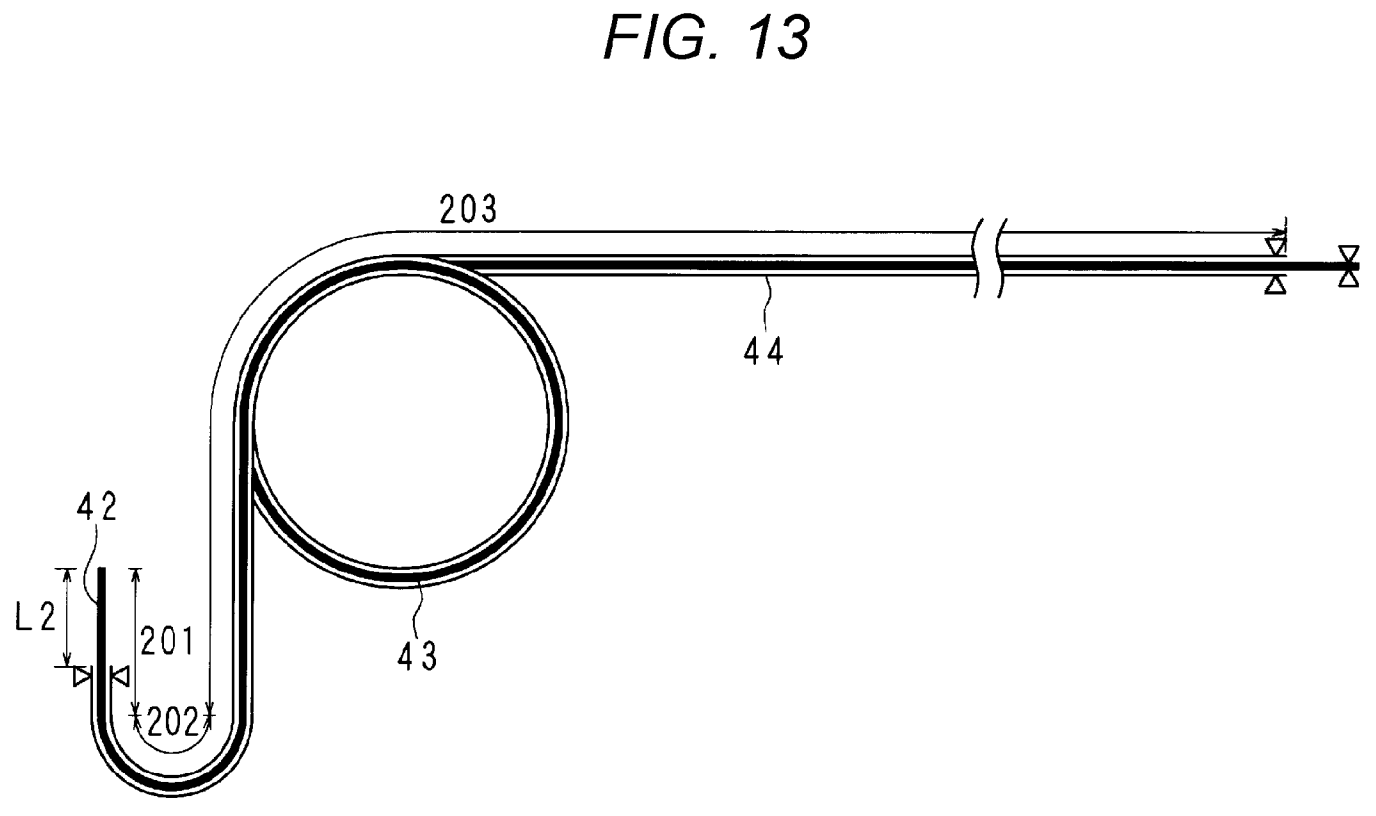

FIG. 13 is a schematic view of the operation coil 43 and the protection coil 44 when the insertion portion 2 is curved and loops.

FIG. 13 schematically illustrates the operation coil 43 and the protection coil 44 when the bending portion 202 of the insertion portion 2 is curved and the soft portion 203 of the insertion portion 2 loops in the middle.

In FIG. 12, when the bending portion 202 of the insertion portion 2 is straightened and the soft portion 203 of the insertion portion 2 is bent in the middle, the wire 42 connected from the distal end portion of the protection coil 44 to the operation coil 43 protrudes by a protrusion amount L1.

As illustrated in FIG. 13, when the bending portion 202 of the insertion portion 2 is curved and the soft portion 203 of the insertion portion 2 is looped in the middle, the wire 42 connected from the distal end portion of the protection coil 44 to the operation coil 43 protrudes by a protrusion amount L2.

When the slider 41 is removed from the operation coil 43 and the experiment is performed, the protrusion amount L2 is slightly shorter than the protrusion amount L1. In this case, the difference between the protrusion amounts L1 and L2 is 0.5 mm or less.

When the slider 41 is connected to the operation coil 43, the frictional force generated when the slider 41, the cam 38, and the movable optical frame 37 each slide suppresses the operation coil 43 from advancing or retreating. Therefore, it is considered that the protrusion amount L2 is substantially equal to the protrusion amount L1 (the movable optical frame 37 is hardly displaced in position).

When the entire operation coil 43 is replaced with a wire similar to the wire 42, the protrusion amount L2 is significantly shorter than the protrusion amount L1, and the difference between the protrusion amounts L1 and L2 is about 10 mm. That is, the movable optical frame 37 is significantly displaced.

The reason for this is described below.

As the insertion portion 2 bends, the protection coil 44 also bends. The outer peripheral side of the curved protection coil 44 extends relative to the inner peripheral side. The wire also bends inside the protection coil 44. Since the wire has no elasticity, the wire is largely pulled inside the protection coil 44 toward the proximal end side of the protection coil 44 as the protection coil 44 bends. Therefore, when the movable optical frame 37 is connected to this wire, the movable optical frame 37 is largely displaced toward the distal end side.

On the other hand, in the case of the operation coil 43, the operation coil 43 also bends inside the curved protection coil 44 as the insertion portion 2 bends. Since the operation coil 43 has elasticity, the outer peripheral side of the operation coil 43 extends relative to the inner peripheral side, similarly to the protection coil 44. That is, since the operation coil 43 also extends at the same time as the extension of the protection coil 44, it is suppressed that the protection coil 44 is pulled into the inside of the protection coil 44.

When the bending of the insertion portion 2 is released, the operation coil 43 and the protection coil 44 each contract at the same time, so that the protection coil 44 is suppressed from protruding from the distal end portion of the protection coil 44.

That is, when the insertion portion 2 is bent, the position of the operation coil 43 in the axial length direction is suppressed from being relatively displaced from the protection coil 44.

Therefore, it is possible to suppress the displacement of the movable optical frame 37 due to the bending of the insertion portion 2.

Since the displacement of the movable optical frame 37 is suppressed, unnecessary changes in the focal length are suppressed.

The imaging unit 3 as described above is built in the insertion portion 2 so that the objective lens 341 of the objective case 31 is exposed from the opening 243 (see FIG. 1) of the cap 24.

The user of the endoscope 1 illustrated in FIG. 1 inserts the insertion portion 2 into the digestive tract from the distal end side. The soft portion 203 flexibly deforms according to the shape of the digestive tract.

The user bends the bending tube 22 by operating the operation knob 111. As a result, the bending portion 202 is bent, so that the distal end portion 201 of the insertion portion 2 faces in the direction desired by the user.

The light emitted by the above-mentioned light source illuminates the inside of the digestive tract.

The image sensor 361 images the inside of the digestive tract. More specifically, the light reflected on the inside of the digestive tract passes through the objective lens 341, the objective lens 342, the objective lenses 344, 344, . . . , and the objective lens 343 in this order, and enters the image sensor 361. The image sensor 361 outputs an electric signal corresponding to the incident light to the driver IC 362. The driver IC 362 outputs the input electric signal to the outside of the endoscope 1 (for example, a display device) via the cable 363 and the connector unit 121.

The display device displays an image corresponding to the input electric signal. The displayed image shows the inside state of the digestive tract. The user observes the inside state of the digestive tract by visually recognizing the displayed image.

The user inserts a treatment tool (not illustrated) from the channel inlet 114 via the forceps plug 113 of the operation unit 11. The distal end portion of the treatment tool passes through the above-mentioned channel tube, and goes from the channel outlet 241 of the cap 24 to the inside of the digestive tract. The user performs appropriate treatment (for example, collection of a sample) using the treatment tool while observing the inside state of the digestive tract.

Due to the urging force of the operation coil 43, the movable optical frame 37 is usually located at the proximal end of the movable range. Therefore, the objective lenses 344, 344, . . . held in the movable optical frame 37 are farthest away from the objective lenses 341 and 342 on the distal end side of the insertion portion 2. Therefore, since the focal length is the shortest, the image sensor 361 can image the widest range (a wide image can be obtained).

Since the operation coil 43 also serves as a spring for urging the movable optical frame 37, for example, it is not necessary to separately arrange a spring for urging the movable optical frame 37 around the movable optical frame 37. Therefore, the number of parts is reduced. In addition, the imaging unit 3 (and thus the endoscope 1) can be miniaturized.

When the user operates the operation lever 112 to one side, the movable optical frame 37 advances toward the distal end of the movable range. Therefore, the objective lenses 344, 344, . . . held in the movable optical frame 37 approach the objective lenses 341 and 342 on the distal end side of the insertion portion 2. Therefore, since the focal length becomes long, the image sensor 361 can magnify a narrow range and take an image (a teleimage can be obtained).

When the user operates the operation lever 112 to the other side, the movable optical frame 37 automatically retracts due to the urging force of the operation coil 43. That is, since the operation coil 43 has the force required to retract the movable optical frame 37, it is not necessary for the user to operate the operation lever 112 to press the operation coil 43.

The user adjusts the focal length by operating the operation lever 112 while visually recognizing the displayed image. As a result, the zoom magnification is adjusted.

When the user is not operating the operation lever 112, that is, when the movable optical frame 37 is stopped without advancing or retreating, for example, even if the user bends the bending tube 22 by operating the operation knob 111, the movable optical frame 37 is unlikely to be displaced. Similarly, even if the soft portion 203 is bent, the movable optical frame 37 is unlikely to be displaced.

The endoscope 1 is not limited to those used in the medical field.

In the embodiment, the movable optical frame 37 is advanced by pulling the operation coil 43, but the movable optical frame 37 may be advanced by pushing the operation coil 43. However, since the operation coil 43 to be pressed is easily bent, it is desirable to pull the operation coil 43. When the operation coil 43 is pulled, the force required for advancing the movable optical frame 37 can be reliably transmitted.

In the embodiment, the forward (forward rotation of the cam 38)/backward (reverse rotation of the cam 38) movements of the operation coil 43 are linked to the forward/backward movements of the movable optical frame 37, but the forward (forward rotation of the cam 38)/backward (reverse rotation of the cam 38) movements of the operation coil 43 may be linked to the backward/forward movements of the movable optical frame 37. Depending on the orientation of each of the cam grooves 381, 381, and 382 provided in the cam 38, the forward (or backward) of the operation coil 43 and one (or the other) of the forward and backward movements of the movable optical frame 37 can be linked.

The operation coil 43 may urge the movable optical frame 37 in the forward direction.

The pitch of the operation coil 43 and the pitch of the protection coil 44 may be different from each other. However, when the pitches of the two are equal, the strands of the operation coil 43 are likely to engage with the strands of the protection coil 44. Therefore, it is possible to further suppress the displacement of the operation coil 43 in the axial length direction of the protection coil 44.

In the embodiment, a case where the zoom magnification changes according to the advancing/retreating of the movable optical frame 37 is described, but the present invention is not limited to this. The endoscope 1 may be configured so that the focusing range (the range in focus on the screen) changes according to the advancing and retreating of the movable optical frame 37.

Second Embodiment

Figure 14:
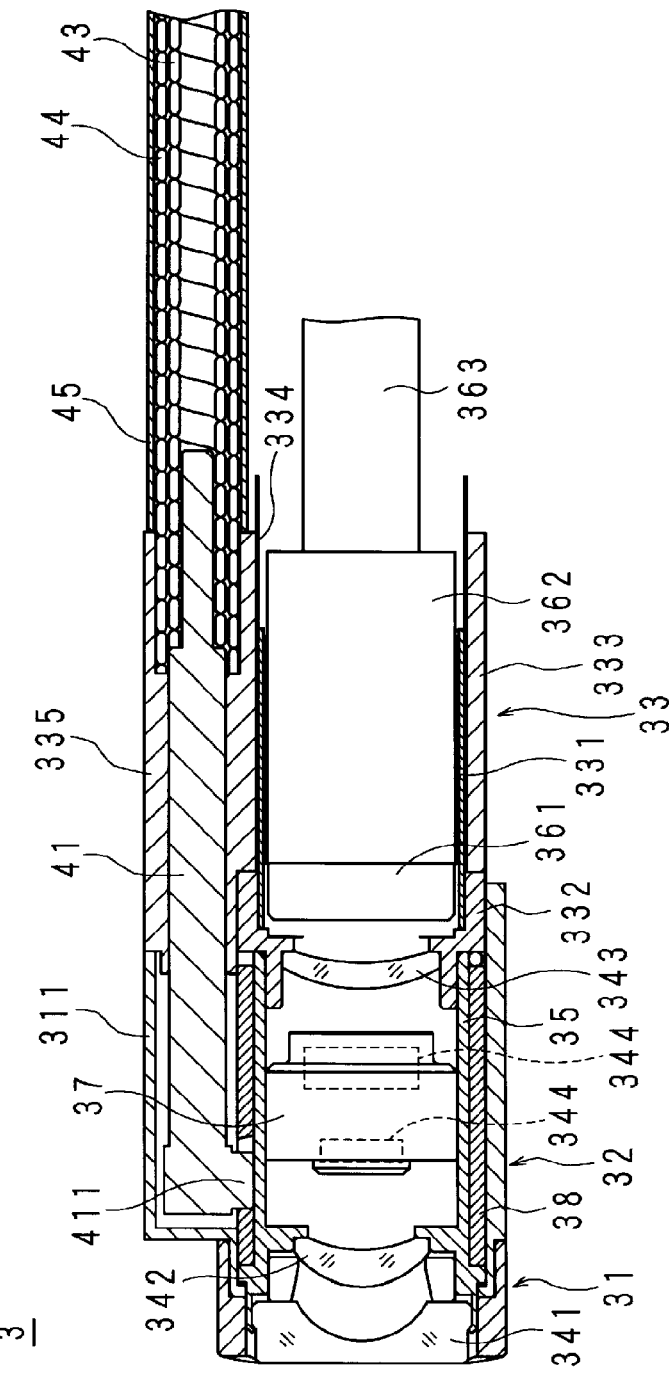
FIG. 14 is a cross-sectional view of the imaging unit of the endoscope according to a second embodiment.

FIG. 14 is a cross-sectional view of the imaging unit 3 of the endoscope 1 according to a second embodiment.

The configuration of the endoscope 1 of this embodiment is substantially the same as the configuration of the endoscope 1 of the first embodiment. The endoscope 1 of this embodiment has substantially the same effect as that of the endoscope 1 of the first embodiment. In the following, the differences from the first embodiment will be described, and the same components as those in the first embodiment are designated by the same reference numerals and the description thereof will be omitted.

The operation coil 43 of the first embodiment is connected to the slider 41 via a wire 42, but the operation coil 43 of this embodiment is directly connected to the slider 41.

Figure 15:
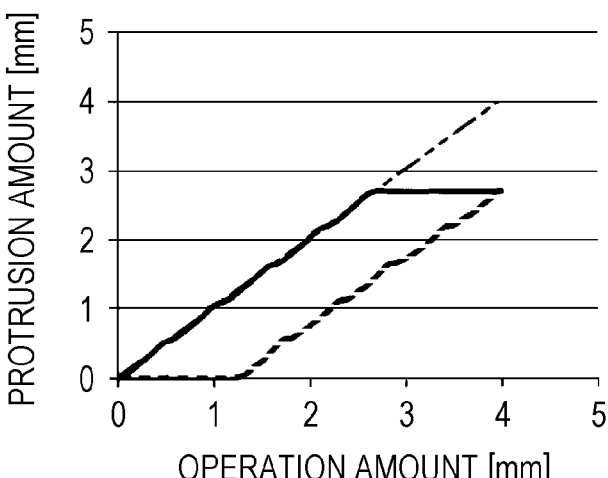
FIG. 15 is a graph illustrating the protrusion amount of an operation member when the operation member inserted into a protection member is moved forward and backward.

FIG. 15 is a graph illustrating the protrusion amount of the operation member when the operation member inserted in the protection member is moved forward and backward.

Here, the protection member is a tightly wound coil having the same configuration as the protection coil 44. The operation member is a tightly wound coil having the same configuration as the operation coil 43. The total length of the operation member is 1800 mm. The operation member is inserted into the protection member, and both end portions of the operation member project from both end portions of the protection member. Both are curved and looped as illustrated in FIG. 13. Both end portions of the protection member are fixed.

The operation member is subjected to an advance operation of pushing the proximal end of the operation member into the protection member, and then a retreat operation of pulling out the proximal end of the operation member from the protection member. The horizontal axis illustrated in FIG. 15 is the operation amount [mm]. The protrusion amount of the operation member is measured during the advancing/retreating operation with the protrusion amount before the advancing/retreating operation as a reference (0 mm). The vertical axis illustrated in FIG. 15 is the protrusion amount [mm].

Ideally, the amount of advancing/retreating operation of the proximal end of the operation member and the protrusion amount of the proximal end of the operation member match (two-dot chain line illustrated in FIG. 15).

In FIG. 15, the protrusion amount during the advance operation is indicated by a broken line.

Even if the proximal end of the operation member is pushed into the protection member, the protrusion amount of the operation member does not change up to 1.3 mm. It is considered that this is because the operation member contracts, so that the force for making the distal end portion of the operation member move forward is not transmitted to the distal end portion of the operation member.

When the advance operation amount exceeds 1.3 mm, the protrusion amount of the proximal end of the operation member linearly increases with the advance operation. When the proximal end of the operation member is pushed in by 4.0 mm, the distal end portion of the operation member protrudes by 2.7 mm.

In FIG. 15, the protrusion amount during the retreat operation is illustrated by a solid line.

Even if the proximal end of the operation member is pulled out from the protection member after being pushed in by 4.0 mm, the protrusion amount of the operation member does not change up to 1.3 mm. It is considered that this is because the operation member extends and the force for making the proximal end of the operation member retract is not transmitted to the proximal end of the operation member.

When the retreat operation amount exceeds 1.3 mm, the protrusion amount of the proximal end of the operation member linearly decreases with the retreat operation. When the proximal end of the operation member is pulled out by 4.0 mm, the protrusion amount of the proximal end of the operation member is 0.0 mm.

From the above, when all the operation members are tightly wound coils, the transmission efficiency (Protrusion amount/Advancing/retreating operation amount×100) is 70%.

By the way, in the actual machine of the endoscope 1, the maximum traction amount of the operation coil 43 by the operation lever 112 is about 10 mm, and the maximum movement amount of the slider 41 is about 5 mm. Therefore, if the transmission efficiency exceeds 50%, it is practical.

That is, in the case of the endoscope 1 of this embodiment, the displacement of the movable optical frame 37 due to the bending of the insertion portion 2 can be suppressed, and the movable optical frame 37 can be sufficiently advanced and retracted.

However, since the operation coil 43 is less likely to bend than the wire, a large force is required to bend the bending portion 202.

Further, especially when the bending portion 202 is greatly bent, it is considered that the contact area between the operation coil 43 and the protection coil 44 is large. However, the frictional force of the operation coil 43 with respect to the protection coil 44 is larger than the frictional force of the wire. The large frictional force is advantageous for suppressing the displacement of the movable optical frame 37, but is disadvantageous for the smooth advancing/retreating of the slider 41 (accordingly the movable optical frame 37).

Figure 16:
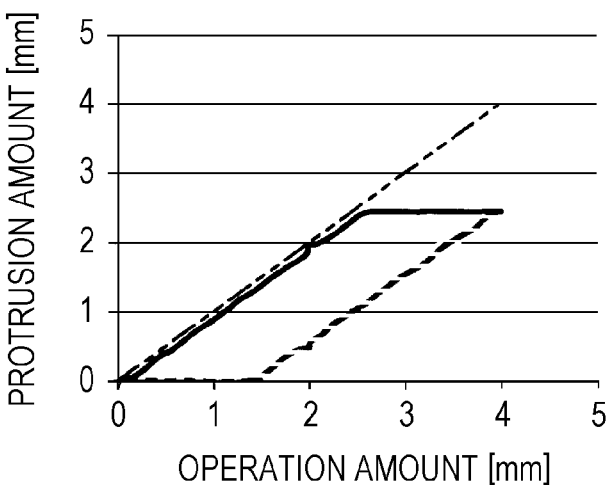
FIG. 16 is a graph illustrating the protrusion amount of the operation member when the operation member (120 mm wire) inserted in the protection member is moved forward and backward.
Figure 17:
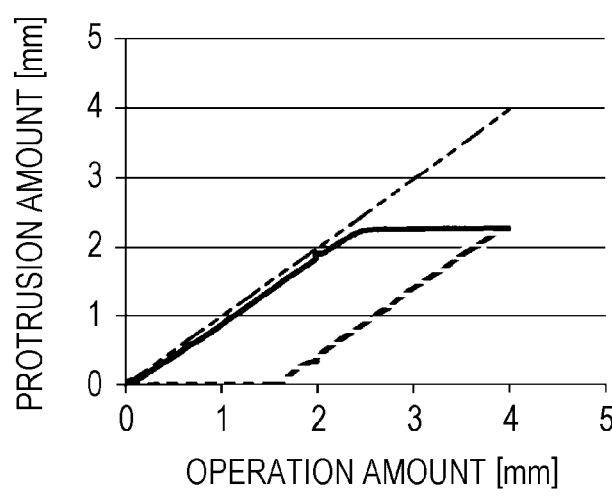
FIG. 17 is a graph illustrating the protrusion amount of the operation member when the operation member (150 mm wire) inserted in the protection member is moved forward and backward.

FIG. 16 and FIG. 17 are graphs illustrating the protrusion amount of the operation member when the operation member inserted in the protection member is moved forward and backward.

Here, the operation member is a tightly wound coil having the same configuration as the operation coil 43 connected to a wire having the same configuration as the wire 42. In the case of FIG. 16, the 120 mm portion on the distal end side of the operation member is the wire. In the case of FIG. 17, the 150 mm portion on the distal end side of the operation member is the wire. These wires correspond to the wires 42 penetrating the bending portion 202 in the endoscope 1 of the first embodiment.

When the advancing/retreating operation has been performed on such an operation member, the change in the protrusion amount at the distal end portion of the operation member has been substantially the same as the change in the protrusion amount illustrated in FIG. 15.

However, for the 120 mm wire, when the proximal end of the operation member is pushed in by 4.0 mm, the proximal end of the operation member protrudes by 2.4 mm. The transmission efficiency is 60%.

For the 150 mm wire, when the proximal end of the operation member is pushed in by 4.0 mm, the proximal end of the operation member protrudes by 2.3 mm. The transmission efficiency is 58%.

When the distal end side of the operation member is replaced with a wire, the transmission efficiency is lowered as compared with the case where all of the operation member is a tightly wound coil. However, as long as the wire length is set appropriately, practical transmission efficiency can be obtained.

That is, also in the case of the endoscope 1 of the first embodiment, the displacement of the movable optical frame 37 due to the bending of the insertion portion 2 can be suppressed, and the movable optical frame 37 can be sufficiently advanced and retracted.

Moreover, since the wire 42 is more easily bent than the operation coil 43, the force required for bending the bending portion 202 can be reduced.

Further, since the frictional force of the wire 42 with respect to the protection coil 44 is small, the movable optical frame 37 can be smoothly moved forward and backward.

As a result of the above, the endoscope 1 of the first embodiment has an advantage of improving operability.

By the way, the wire 42 is easily contacted with the protection coil 44 and is arranged in the bending portion 202 having a relatively short distance, and the operation coil 43 is arranged in the soft portion 203 having a long distance. Therefore, there is no possibility that the small frictional force of the wire 42 causes the displacement of the movable optical frame 37.

REFERENCE SIGNS LIST

1 endoscope
11 operation unit
112 operation lever (traction portion)
2 insertion portion
201 distal end portion
202 bending portion
203 soft portion
37 movable optical frame
38 cam
42 wire
43 operation coil
44 protection coil

The invention claimed is:

1. An endoscope, comprising:

an insertion portion that includes a distal end portion, a bending portion, and a soft portion in order from the distal end side;

a movable optical frame that is built in the distal end portion and capable of advancing and retreating in an axial length direction of the insertion portion;

an elastic operation coil that is connected to the movable optical frame via a slider connected to a distal end of a wire and capable of advancing and retreating in the axial length direction of the insertion portion, wherein:

when the operation coil is pulled and retreated by an operation of an operation lever, a force with which the movable optical frame advances is less than a force with which the movable optical frame retreats when the operation coil advances, and within the soft portion, a proximal end of the wire is inserted into and fixed to the operation coil; and a protection coil through which the operation coil is inserted and which penetrates at least the bending portion.

2. The endoscope according to claim 1, wherein the wire has an outer diameter smaller than an outer diameter of the operation coil.

3. The endoscope according to claim 1, wherein the operation coil and the movable optical frame are connected via a tubular cam surrounding the movable optical frame, and advancing/retreating of the operation coil, forward/reverse rotation of the cam in a circumferential direction, and advancing/retreating of the movable optical frame are linked.

4. The endoscope according to claim 1, wherein a pitch of the operation coil is equal to a pitch of the protection coil.

5. The endoscope according to claim 1, wherein advancing/retreating of the operation coil corresponds to retreating/advancing of the movable optical frame, and wherein the operation coil urges the movable optical frame in a backward direction.

6. The endoscope according to claim 5, wherein the operation lever is provided in an operation unit to which a proximal end side of the soft portion is connected.

7. The endoscope according to claim 1, wherein a strand of the operation coil is a flat wire.

8. The endoscope according to claim 1, wherein the operation coil is a wound coil.

9. The endoscope according to claim 8, wherein the protection coil is a wound coil, and wherein a strand of the operation coil and a strand of the protection coil are the same as each other.

10. The endoscope according to claim 1, wherein the protection has elasticity such that when the bending portion is bent, the protection coil and the operation coil are also bent.

11. The endoscope according to claim 1, further comprising a slider guide having a through hole through which the slider is slidably inserted.

12. The endoscope according to claim 1, wherein a distal end portion of the protection coil is fixed to the slider guide.

* * * * *